United States Patent [19]

Carrington

[11] 4,109,657
[45] Aug. 29, 1978

[54] BODY PROFILED SURGICAL DRAINAGE APPLIANCE

[76] Inventor: Russell Settle Carrington, 6804 Atwood St., District Heights, Md. 20028

[21] Appl. No.: 733,921

[22] Filed: Oct. 19, 1976

[51] Int. Cl.$^2$ ............................................. A61F 5/44
[52] U.S. Cl. ................................................... 128/283
[58] Field of Search ....................... 128/283, DIG. 24

[56] References Cited
U.S. PATENT DOCUMENTS

| | | | |
|---|---|---|---|
| 3,826,262 | 7/1974 | Blackwood | 128/283 |
| 3,841,332 | 10/1974 | Treacle | 128/283 |
| 3,878,847 | 4/1975 | Marsan | 128/283 |
| 3,964,485 | 6/1976 | Neumeier | 128/283 |

*Primary Examiner*—Robert W. Michell
*Assistant Examiner*—Michael H. Thaler
*Attorney, Agent, or Firm*—Lowe, King, Price & Markva

[57] ABSTRACT

An appliance for supporting a fecal bag to the body of a colostomy or ileostomy patient to receive bodily discharge from the stoma comprises an ellipsoidal plate having a curved surface on a body engaging side and a recessed bag supporting ring on the opposite side. The outer rim of the plate along its major axis is arced to conform to body profile. A central aperture formed in the plate extends through the ring for positioning the stoma in the fecal bag. The plate is attached to the body using an appliance belt, and the curved body engaging surface pushes the skin inwardly at the abdominal opening to cause the stoma to be maintained in an extended position for drainage into the bag. The curved body engaging surface also increases the surface contact area between the plate and body and improves the plate-to-body seal. This prevents leakage of bowel acids under the plate, and minimizes slippage. The curved profile of the plate and recessed ring member for supporting the bag make the appliance virtually undetectable when worn under clothing.

8 Claims, 3 Drawing Figures

U.S. Patent  Aug. 29, 1978  4,109,657
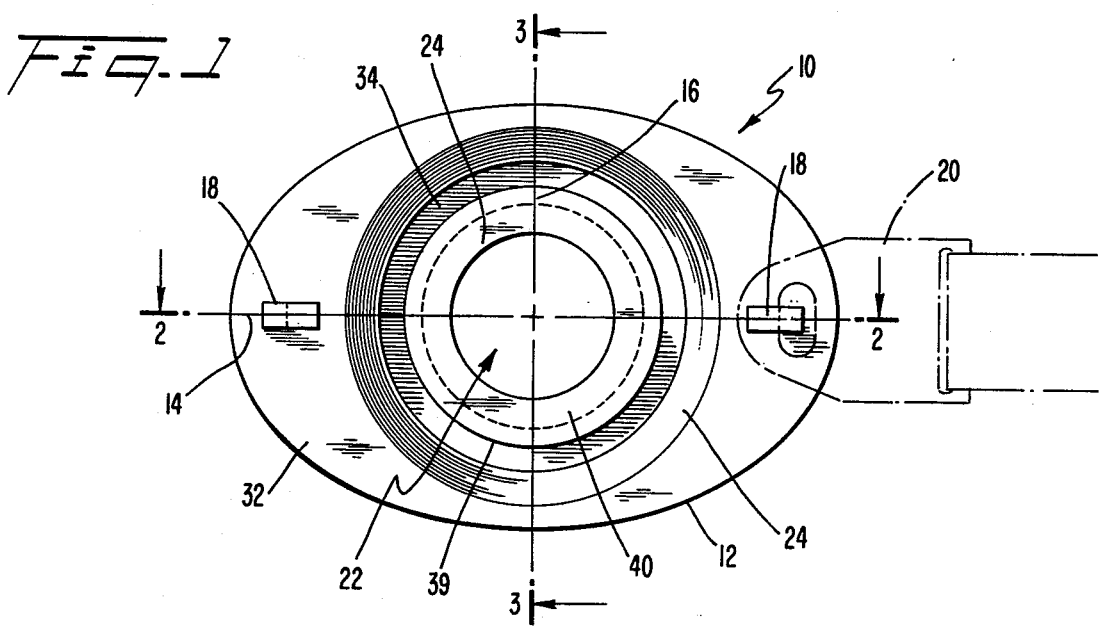
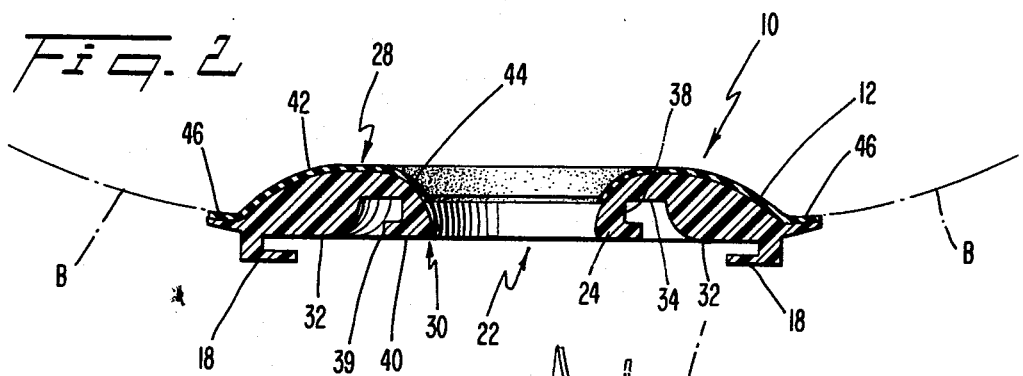
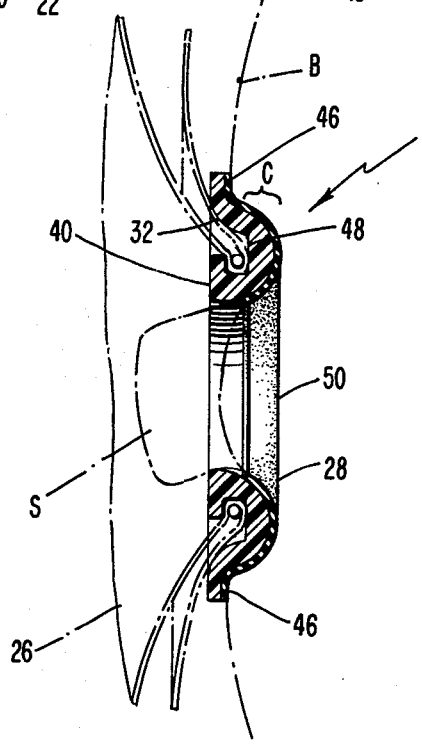

BODY PROFILED SURGICAL DRAINAGE APPLIANCE

BACKGROUND OF THE INVENTION

This invention relates generally to surgical drainage devices for colostomys or ileostomys, and more particularly, toward such devices that are compact and more securely sealed to the skin, and are compact and unobtrusive when worn under clothing.

Following the creation of an ostomy, such as a colostomy or ileostomy, wherein an artificial anus is provided by making an opening from the colon or ileum through the abdominal wall, bowel fluid drained from the stoma is collected in a fecal bag. This collection process may be either a temporary post-operative procedure or permanent.

Typically, the fecal bag is supported to the stoma by a surgical drainage appliance that is mounted to the outer wall of the abdomen around the stoma using an appliance belt and glue. The body engaging surface of the appliance is generally flat and the bag supporting surface contains a raised ring member to which the fecal bag is supported using an elastic band or the like.

While generally somewhat satisfactory, prior ostomy appliances of which I am aware have been uncomfortable, obtrusive when worn under clothing and have caused irritation of the skin. In particular, because the body engaging surfaces of prior applicances are flat, there is minimum contact surface area between skin and appliance. Bowel acids tend to leak between the appliance and skin causing skin irritation. Furthermore, the appliance tends to slip with movement of the stomach during coughing, for example.

Because the ring member for supporting the fecal bag is upstanding on the surface of the appliance, the appliance is noticeable when worn under clothing. The action of clothing pressing the fecal bag against the rim of the ring sometimes causes the mouth of the bag to slip from the ring.

Accordingly, a general object of the invention is to provide a new and improved surgical drainage appliance overcoming the disadvantages of the prior art.

Another object is to provide a new and improved surgical drainage appliance that is compact and conforms to the profile of the body so as to be unnoticeable under clothing.

Another object is to provide a new and improved surgical drainage appliance that is comfortable to wear and does not shift its position on the stomach during movement of stomach portions, such as during coughing.

Yet another object of the invention is to provide a new and improved surgical drainage appliance that has increased contact surface area with the skin and prevents irritation caused by leakage of bowel acids between the appliance and skin.

Still another obeject of the invention is to provide a new and improved surgical drainage appliance that retains the stoma in an extended position for drainage into a fecal bag by pressing the skin inwardly at the abdominal opening.

SUMMARY OF THE INVENTION

In accordance with the present invention, a surgical drainage appliance comprises an ellipsoidal plate member having a curved body engaging surface on one side and a recessed ring member for supporting a fecal bag on the opposite side. A central aperture is formed in the plate member for retaining the stoma in position through the surgically created abdominal opening for drainage into a fecal bag.

The bag supporting side of the plate includes a substantially flat surface portion containing a circular channel adjacent the central aperture. The recessed ring member is formed in the channel for supporting the fecal bag around the stoma. The exposed end of the ring member extends toward, but not beyond, a plane defining the flat surface portion of the plate.

The surface of the body engaging side of the plate curves inwardly toward the body engaging side of the plate and forms the wall of the central aperture. The curved surface at the central aperture (1) tends to retain the stoma in an extended position for drainage into the fecal bag by pushing the skin inwardly around the stoma of the abdominal opening, and (2) provides increased surface contact area with the skin so that there is a better seal for preventing leakage of bowel acids under the plate, and less likelihood of slippage.

The ellipsoidal shape of the plate is defined by a major axis and a minor axis. The outer rim of the plate along the minor axis is flat. The outer rim of the plate along the major axis, on the other hand, is arced inwardly toward the body to conform with the body profile. The arced profile of the plate in combination with the recessed ring member for supporting the fecal bag makes the appliance virtually impossible to detect when worn under clothing.

The bag supporting side of the appliance contains a pair of brackets along the major axis of the plate. The brackets attach to the ends of a conventional appliance supporting belt. If desired, the body engaging side of the plate can be coated with a layer of glue to improve contact with the skin.

The plate member is preferably formed of nylon so as to be somewhat flexible, and may contain a layer of soft pad material, such as rubber or polystyrene, on the body engaging side.

Still other objects and advantages of the present invention will become readily apparent to those skilled in this art from the following detailed description, wherein I have shown and described only the preferred embodiment of the invention, simply by way of illustration of the best mode contemplated by me of carrying out my invention. As will be realized, the invention is capable of other and different embodiments, and its several details are capable of modification in various obvious respects, all without departing from the invention. Accordingly, the drawings and description are to be regarded as illustrative in nature, and not as restrictive.

BRIEF DESCRIPTION OF THE DRAWING

FIG. 1 is a top view of an appliance in accordance with the invention, supported to a body with an appliance belt;

FIG. 2 is a cross-sectional side view of the appliance of FIG. 1 taken along the line 2—2; and FIG. 3 is a cross-sectional side view of the appliance of FIG. 1 taken along the line 3—3, with a fecal bag mounted using a resilient band.

DETAILED DESCRIPTION OF A PREFERRED EMBODIMENT

Referring to FIG. 1, a surgical drainage appliance 10, in accordance with the invention, comprises an approximately ellipsoidal plate 12 defined by a major axis 14 and a minor axis 16. A pair of brackets 18 are located on the major axis 14 of plate 12 for attachment to the ends of an appliance belt 20 (only one end of the belt is shown). A central aperture 22 is formed in the plate 12 for placement around the stoma S (FIG. 3) at a surgically created abdominal opening (not numbered). A recessed, upstanding ring member 24, discussed in detail below, is formed on the plate 12 adjacent central aperture 22 for supporting a fecal bag 26 (FIG. 3).

Plate 12 preferably is formed of nylon or other durable material that is lightweight and slightly flexible. An optional layer of padding 50 (FIG. 3), such as rubber or polystyrene, may be located on the body engaging side 28 of the plate 12.

Referring to FIG. 2, plate 12 is seen to include a body engaging side 28 and a bag supporting side 30. Bag supporting side 30 has a substantially flat, annular portion 32 that curves inwardly toward side 28 forming an annular channel 34, as shown. The inner wall of channel 34 defines the recessed, upstanding ring member 24. An annular recess 38 is located in the exposed outer wall of ring member 24. Recess 38 defines a flange 39 for supporting the mouth of fecal bag 36 (FIG. 3). Of particular importance, the exposed end 40 of ring member 24 extends not beyond, and is preferably flush with, a plane defining the flat surface portion 32 of plate 12.

Still referring to FIG. 2, the body engaging side of plate 12 is gently curved away from the body B, as indicated at 42, toward outer rim 46 of the plate 12, and is more steeply curved toward aperture 22, indicated at 44, therefore defining the wall of said aperture. Since the outer surface of side 28 is curved at the central aperture 22, pressure on the stoma by the aperture wall is minimized. The curved profile of the surface of side 28 also houses the channel 34 which is recessed with respect to the surface of the opposite side 28.

Ring member 24, which is integral to the plate 12, besides functioning as a support for fecal bag 26, also increases the strength and rigidity of the plate in the region of central aperture 22. The annular recess 38, formed in the exposed side of the ring 24, receives an elastic band 48 (FIG. 3) for supporting the mouth of bag 26 to the plate 12.

The outer rim 46 of plate 12 along major axis 14 (see FIG. 2) is curved toward the body to conform with the body profile. The rim 46 along the minor axis 16 of plate 12 (see FIG. 3), on the other hand, is formed along an approximately straight line, as shown.

Referring to FIG. 3, the drainage appliance 10 is shown attached to the body B of a patient using belt 20 (not shown in FIG. 3). The mouth of fecal bag 26 is supported to ring member 24 at flange 39 with a conventional elastic band 48 seated within recess 38. Stoma S extending through the surgically created abdominal opening, as shown, is positioned within the mouth of bag 26 through central aperture 22 of plate 12.

Of particular importance, the curved profile of body engaging side 28 of plate 12 presses the skin toward the abdomen at the abdominal opening, as shown, tending to extend stoma S into proper position for drainage of bowel fluids into bag 26. The large surface contact area between side 28 of plate 12 and the skin of the patient increases friction between the skin and plate and prevents slippage of the plate, even during movement of portions of the stomach during coughing, for example. Furthermore, since the skin tends to conform to the profile of the side 28 of the plate 12, there is no leakage of bowels acids between the plate and skin, so that irritation of the skin is minimized.

Still referring to FIG. 3, end 40 of ring member 24 extends outwardly from plate 12 up to, but not beyond, the plane of the flat portion 32 of the plate. Since the surface of side 28 is curved, plate 12 tends to form a "cavity" c (FIG. 3) in the surface of the skin when the plate is mounted to the body with belt 20. Thus, the recessed ring member 24 does not extend substantially beyond the normal surface of the skin and the plate is virtually undetectable when worn under clothing. In addition, the plate 12 is undetectable because the inwardly curved rim 46 in major axis 14 (FIG. 2) causes plate 12 to conform to the profile of the body.

In this disclosure, there is shown and described only the preferred embodiment of the invention, but, as aforementioned, it is to be understood that the invention is capable of use in various other combinations and is capable of changes or modifications within the scope of the inventive concept as expressed herein.

What is claimed is:

1. A body profiled, surgical drainage appliance to be worn by a user, comprising:
   a plate member having a body engaging side and a bag supporting side, said member including a central aperture for receiving a stoma extending through a surgically created abdominal opening;
   said bag supporting side including a substantially flat surface portion defining a plane and having an annular channel formed therein around said central aperture;
   an integral ring member totally recessed into the bag supporting side of said plate member and defining one wall of said annular channel, said ring member having an annular flange for supporting a fecal bag around said stoma, said flange having an outer end parallel to said plane, said outer end of said flange extending toward but not beyond said plane;
   said body engaging side of said plate member and the wall of said central aperture being defined by a continuously curved, body engaging surface to accommodate said channel within said plate member, said curved surface being operative to press skin inwardly at the abdominal opening for retaining the stoma in an extended position for drainage of body fluids into said bag, the flange of said ring member extending outwardly from the body of the user, when worn, within the natural contour of the user's body; and
   means for mounting said plate member to the body of the user.

2. The appliance of claim 1, wherein said plate member is approximately ellipsoidal defined by a major axis and a minor axis.

3. The appliance of claim 2, wherein said plate member has an outer rim that is flat along the minor axis, and inwardly curved along the major axis to conform to body profile.

4. The appliance of claim 2, wherein said mounting means includes a pair of bracket members on the bag supporting side of said plate member along the major axis thereof for attachment to the ends of an appliance supporting belt.

5. The appliance of claim 1, wherein said plate member is formed of nylon.

6. The appliance of claim 5, wherein the body engaging side of said plate member includes a layer of soft pad material.

7. The appliance of claim 1, wherein the outer end of said flange is coplanar with said substantially flat surface portion of said plate member.

8. The appliance of claim 1, wherein said curved surface has a radius small enough to provide, when worn by the user, substantially continuous contact between the curved body engaging surface of the appliance and the body, including a portion of the stoma, of said user.

* * * * *